(12) United States Patent
Shah et al.

(10) Patent No.: US 8,097,581 B2
(45) Date of Patent: Jan. 17, 2012

(54) ANTI-WRINKLE COSMETIC COMPOSITION

(75) Inventors: Amit R. Shah, Commack, NY (US); John L. Gormley, Midland Park, NJ (US); George P. Majewski, Redondo Beach, CA (US)

(73) Assignee: Grant Industries Inc., Elmwood Park, NJ (US)

( * ) Notice: Subject to any disclaimer, the term of this patent is extended or adjusted under 35 U.S.C. 154(b) by 610 days.

(21) Appl. No.: 12/119,065

(22) Filed: May 12, 2008

(65) Prior Publication Data
US 2009/0136595 A1  May 28, 2009

Related U.S. Application Data

(60) Provisional application No. 60/928,624, filed on May 10, 2007.

(51) Int. Cl.
*A61K 33/24* (2006.01)
*A61K 38/00* (2006.01)

(52) U.S. Cl. .......................................... 514/1.1; 424/649

(58) Field of Classification Search .......................... None
See application file for complete search history.

(56) References Cited

U.S. PATENT DOCUMENTS

| | | | |
|---|---|---|---|
| 4,814,173 A * | 3/1989 | Song et al. | 424/444 |
| 6,875,744 B2 * | 4/2005 | Owen | 514/3.3 |
| 2006/0257437 A1 * | 11/2006 | Ingman | 424/401 |

OTHER PUBLICATIONS (Grant Industries, Inc., website—Internet Archives as of May 26, 2006; pp. 1-3 (attached), last accessed Jun. 6, 2011).*
(Grant Industries, Inc., website—Internet Archives as of Mar. 1, 2006; p. 1 (attached), last accessed Jun. 6, 2011).*
Dos Santos et al., (J. Mater. Chem. Epub Jun. 15, 2005,15:3045-3049).*
Tashtoush et al., (J Pharm Biomed Anal. Feb. 19, 2007;43(3):893-9. Epub Oct. 16, 2006).*
(web = laroccaskincare.com/products/cleanser; last accessed Jun. 6, 2011).*

* cited by examiner

*Primary Examiner* — Cherie M Woodward
(74) *Attorney, Agent, or Firm* — Jonathan Myers; Andrew Wilford

(57) ABSTRACT

The present invention relates to a composition for treating skin comprising an acylated short chain bioactive peptide and fulvic acid, and optionally colloidal gold. The invention further relates to a method for topically administering the composition in an amount therapeutically effective to reduce wrinkles by building the dermal fibroblast matrix. The invention further relates to a method of treating wrinkled skin by topically administering the composition to an individual in need of such treatment.

2 Claims, No Drawings

ANTI-WRINKLE COSMETIC COMPOSITION

CROSS REFERENCE TO RELATED APPLICATION

This application is related to provisional application 60/928,624 filed 10 May 2007.

FIELD OF THE INVENTION

This invention relates to a composition of acylated oligopeptide and aqueous fulvic acid extract product for treatment of fine lines and wrinkles in facial skin by improving fibroblast matrix and a method of using the composition. Preferably, the acyl oligopeptide is a palmitoyl hexapeptide based on the amino acids phenylalanine, alanine, leucine and lysine. The fulvic acid is the water-soluble fraction of acidified humus, obtained from naturally occurring peat. The composition may contain dimethylisosorbide or ethoxydiglycol as solubilizing and penetration enhancers for the acyl-modified oligopeptide and other preferred skin beneficial ingredients.

BACKGROUND OF THE INVENTION

U.S. Pat. No. 6,875,744 B2 specifies short bioactive peptides that are primarily made from phenylalanine, alanine, leucine and lysine. Such peptides are water soluble or miscible and have been reported to offer a low in-vitro minimum inhibitory concentration (MIC) against *P. acnes*. Benefits for hydrophobic acylated peptides of similar sequences have been reported include increasing cell density of fibroblast cells in the Cyquant cell proliferation assay (Molecular probes, C-7026) due to boosting the immune system by acting like a host defense peptide. Host defense peptides boost the innate immune system and have been shown to have a number of immunomodulatory functions including altering host gene expression, acting as chemokines and/or inducing chemokine production, inhibiting lipopolysaccharide induced pro-inflammatory cytokine production, promoting wound healing, and modulating the responses of dendritic cells and cells of the adaptive immune response. The boosting of such aspects of healthy skin are the same as are required for younger and less-wrinkled skin.

It is not generally recommended that such peptides be stored in solution. However, the shelf life of peptides is extended for sequences not containing Cysteine, Methionine, Tryptophan, Asparagine and Glutamine.

Peptides are not very useful if they are insoluble in the aqueous buffers required for testing in bioassay systems. Peptides can be made more lipophilic with C2-C22 alkyl esters or amides on the terminus to modify the interaction of the peptide with skin lipids but this modification drastically changes the solubility and makes peptides even more difficult to deliver in a stable aqueous cosmetic vehicle. Many biochemists use dimethylformamide or dimethylsulfoxide to help dissolve peptides for aqueous bioassay. Both of these solvents are not considered acceptable for cosmetic use. Solvents like ethoxydiglycol or dimethylisosorbide are useful cosmetic solvents for enhancing skin activity and can help solubilize the lipophilic peptide in an oil phase. Formulation of excess lipophilic solvent can remove surface lipids and leave the skin feeling dry or brittle. U.S. Pat. No. 4,814,173 teaches the combination of dimethylisosorbide, peptide and silicone elastomers as part of a preferred transdermal matrix system.

Fulvic acid is the water-soluble fraction of acidified humus. Humus is the naturally occurring decomposition product of vegetation as found in peat sources. Fulvic acid is thought to aid transport of minerals to cells. US application 20060257437 (Ingman) used a combination of water, silica, and optionally silver ions, in a cosmetic containing fulvic acid for concealing wrinkles and improving skin condition, but did not employ peptides in the cosmetic specification.

Commonly assigned application Ser. No. 11/654,406 was filed on 17 Jan. 2007, claims the benefit of the 18 Jan. 2006 filing date of Provisional Application Ser. No. 60/760,034, and is incorporated-by-reference in its entirety. Ser. No. 11/654,406 discloses that specific short chain acylated peptides in combination with lycium barbarum (goji berry) glyco-conjugates lead to improved dermal fibroblast activity, resulting in anti-wrinkle benefits in cosmetic applications.

OBJECTS OF THE INVENTION

It is an object of the invention to provide a cosmetic composition having the capability of rebuilding of the in-vivo skin matrix by synergistically improving dermal fibroblast regulation with ingredients delivered topically.

It is a further object of the invention to provide a cosmetic composition that will maintain the skin in a moist healthy state and maintain the proper skin barrier lipid balance by preparing a composition combining short chain acyl-peptides, fulvic acid and optionally colloidal gold to stimulate the cellular mechanism responsible for the production of dermal collagen and fibroblast growth.

SUMMARY OF THE INVENTION

We have achieved the stated objects by providing a topical cosmetic composition comprised of:
  0.001% to about 0.1% by weight percent of C2-C22 acylated oligopeptide of 3-20 amino acid units; and
  0.01% to about 50% by weight of fulvic acid; and
  0.001 to 0.1% by weight of colloidal gold.

The acylated oligopeptide is preferably solubilized or emulsified in the liquid phase of the cosmetic composition. Preferably, the acylated oligopeptide peptide is first dissolved in ethoxydiglycol or dimethylisosorbide prior to adding combining with other ingredients. About 0% to about 5% emulsifier may be used to stabilize an emulsion form if one is so desired.

The cosmetic may contain inorganic carrier powders to create an essentially dry composition. Inorganic carrier powders include mica, barium sulfate, fumed silica and colloidal sized gold.

The cosmetic composition containing peptide, fulvic acid and colloidal gold may be applied to the skin by a method of massaging in a powdered or liquid cosmetic preparation on the skin surface.

The composition is preferably formulated into a catalytic complex designed to stimulate anti-aging cellular turnover as delivered from loose and pressed powder cosmetics. The peptide, preferably palmitoyl hexpeptide-6, aids matrix-fibroblast stimulation and collagen growth.

Without being bound to theory, fulvic acid (purified from humic acid source) acts as a natural source of minerals and nutrients and colloidal gold may serve to promote electron transfer between fulvic acid minerals and the metal ions in the skin.

The invention further relates to a method of treating wrinkled skin by topically administering the composition to an individual in need of such treatment. The composition containing peptide, fulvic acid and colloidal gold is preferably applied to skin by a method of massaging the composition onto the surface of the skin under uniform pressure.

The cosmetic composition may be delivered in an acceptable vehicle consisting of an emulsion, lotion, spray, aerosol, powder, ointment, cream and foam. Preferably, the composition is a loose powder that entrains any liquid components of the composition.

The preferred oligopeptides include those containing Phe, Ala, Leu and Lys residues and exhibiting dermal fibroblast matrix rebuilding properties. This sequence class is described in U.S. Pat. No. 6,875,744 B2 and the specific sequence most preferred herein is: Phe Ala Leu Leu Lys Leu (SEQ ID NO:1). The entire disclosure of U.S. Pat. No. 6,875,744 B2 is hereby incorporated by reference. The preferred acyl group used to acylate the oligopeptides is an alkanoyl group having 2 to 22 carbon atoms, more preferably 10 to 20 carbon atoms, and a preferred alkanoyl group is palmitoyl. The preferred palmitoyl oligopeptides are palmitoyl tripeptide, palmitoyl tetrapeptide, palmitoyl pentapeptide, palmitoyl hexapeptide, palmitoyl hexapeptide-3, and more preferably a palmitoyl hexapeptide with only the four amino acids phenylalanine, alanine, leucine and lysine in the sequence for increased solution stability, including palmitoyl hexapeptide-6; and still more preferably the sequence FALLKL-NH2 modified with a palmitoyl group. The latter compound is commercially available from Helix Biomedix, Bothell, Wash. under the name HB168PAL.

The acyl group may acylate the N-terminal of the oligopeptide, one of the functional groups on a side chain of an amino acid within the oligopeptide, wherein the functional group is capable of acylation with an acyl group, especially a hydroxy, amino or carbamoyl functional group, or at the C-terminal of the oligopeptide, especially when the C-terminal is amidated wherein the acyl group acylates the amido nitrogen of the amidated C-terminal.

Another preferred group of acylated oligopeptides includes oligopeptides whose N-terminal is acylated with a C2 to C22 acyl group, preferably alkanoyl. The most preferred acyl group is acetyl. A particular preferred compound within this group is commercially available under the name ARGIRELINE7 from Lipotec, Barcelona, Spain. The oligopeptide has the following sequence:

Glu Glu Met Gln Arg Arg (SEQ ID NO:2)

and the structural formula for ARGIRELINE7 is as follows:

Acetyl-Glu Glu Met Gln Arg Arg-NH2.

As will be described more fully, the combination of C2-C22 acylated oligopeptide, fulvic acid and gold colloid was unexpectedly found to be synergistic towards improving the fibroblast matrix.

The acyl-modified oligopeptide is preferably first solubilized in dimethylisosorbide (Arlasolve DMI-Uniqema, New Castle, Del.) or ethoxydiglycol (Transcutol CG-Gattefosse USA, Paramus, N.J.) prior to formulating the peptide into the final cosmetic.

On the occasion when an emulsifier is required for making a stable emulsion, it may be included in both the water and oil phases of the emulsion to best match the requirements of a formula. Surfactant emulsifiers may include, but are not limited to: halide or amino neutralized C12-C20 alkylsulfates, C12-C20 alkylpolyglucosides; mono and di substituted C12-C20 alkylphosphates; ethoxylated fatty alcohols preferably oleth-2, laureth-4, laureth-23, ethoxylated fatty acids like hydrogenated castor oil ethoxylates; and natural ingredients, like saponins or phospholipids (like lecithin). Many commercial choices of surfactant types are available per the McCutcheons emulsifiers guide book and are acceptable herein if they are non-irritating or toxic to the skin and do not impart a poor skin feel. Polymeric emulsifiers like alkoxy-modified polysiloxanes (like Abil series—Degussa), ammonium polyacryloyldimethyl taurate and acrylate copolymers (Simulgel series-Seppic), may also be used.

The compositions of the present invention may also include a safe and effective amount of a penetration enhancing agent. By "safe and effective amount" is meant an amount sufficient to enhance penetration of peptide and fulvic acid into the skin, but not so much as to cause any side effects or skin reactions, generally from about 1% to about 5% of the composition. Besides acting as peptide solvent, dimethylisosorbide and ethoxdiglycol may act as penetration enhancing agents. Examples of other useful penetration enhancers, include a penetration-enhancing vehicle consisting essentially of (a) N-(2-hydroxyethyl)-pyrrolidone and (b) a cell envelope disordering compound selected from methyl laurate, oleic acid, oleyl alcohol, mono-olein, myristyl alcohol, and mixtures thereof, wherein component (a) and (b) are present in a ratio of (a):(b) of about 1:5 to about 500:1 by weight. U.S. Pat. No. 4,557,934 teaches a pharmaceutical composition comprising the penetration enhancing agent 1-dodecylazacycloheptan-2-one, and a penetration enhancing diol or cycloketo compound selected from the group consisting of: 1,2-propanediol, 1,3-propanediol, 1,2-butanediol, pyrrolidone; 1-(2-hydroxyethyl)azacyclopentan-2-one, and mixtures thereof. U.S. Pat. No. 4,130,667 describes a penetration enhancer comprising:

(a) at least about 0.1% by weight of a sugar ester selected from sucrose monooctanoate, sucrose monodecanoate, sucrose monolaurate, sucrose monomyristate, sucrose monopalmitate, sucrose monostearate, sucrose monooleate, and sucrose dioleate; and (b) at least about 0.1% by weight of a phosphine oxide compound selected from octyl or monyl or decyl or undecyl or dodecyl-dimethyl phosphine oxide, and the 2-hydroxydecyl derivative thereof.

It is noteworthy to mention some amphiphilic penetration enhancers also function as co-emulsifier.

The emulsion compositions of the invention may contain, in addition to the above-described components, a wide variety of additional oil-soluble materials and/or water-soluble materials conventionally used in topical compositions, at their art-established levels.

Oil-soluble materials may comprise up to about 50% of the total composition, preferably up to about 30%. The compositions of the present invention can also contain from about 2% to about 50% of at least one cosmetically acceptable emollient. Various types of emollients are known, depending on whether the emollient is in the aqueous or the oil phase of the emulsions. Some emollients listed also contribute to emulsification stability.

As used herein, "emollients" refer to materials used for the prevention or relief of dryness, as well as for the protection of the skin. A wide variety of suitable emollients are known and may be used herein. Sagarin, Cosmetics, Science and Technology, 2nd Edition, Vol. 1, pp., 32-43 (1972), incorporated herein by reference contains numerous examples of suitable materials. Examples of classes of useful emollients include the following:

1. Hydrocarbon oils and waxes. Examples include mineral oil, petrolatum, microcystalline wax, paraffins, polyethylene, perhydrosqualene and hydrogenated polyisobutene. Also included in this group are wax esters such as beeswax, spermaceti, myristyl myristate, stearyl, stearate and the derivatives thereof such as ethoxylated sorbitol beeswax ether-esters. Further included are vegetable waxes including carnauba and candelilla waxes.

2. Volatile polysiloxanes (linear or cyclic), nonvolatile silicone fluids such as polydimethyl siloxanes with viscosities ranging from about 10 to about 100,000 centistokes are 25° C. Methylphenyl, phenyltrimethiconepolysiloxanes, water-soluble and alcohol-soluble silicone glycol copolymers including dimethicone.
3. Triglyceride esters, for example vegetable and animal fats and oils including oils of castor, safflower, primrose, jojoba, cottonseed, corn, cod liver, palm, sesame, and soybean.
4. Acetoglyceride esters, such as acetylated monoglycerides.
5. Ethoxylated glycerides, such as ethoxylated glyceryl monostearate.
6. C1-C20-alkyl esters of fatty acids having 10 to 20 carbon atoms such as laurates, palmitates, oleates, stearates, adipates, sebacates, and lauryl lactates.
7. Alkenyl esters of fatty acids having 10 to 20 carbon atoms. Examples include oleyl myristate, oleyl stearate, and oleyl oleate.
8. Fatty acids having 10 to 20 carbon atoms. Suitable examples include pelargonic, lauric, myristic, palmitic, stearic, isostearic, hydroxystearic, oleic, linoleic, ricinoleic, arachidic, behenic, and eruric acids.
9. Fatty alcohols having 10 to 20 carbon atoms. Lauryl, myristyl, cetyl, hexadecyl, stearyl, isostearyl, hydroxystearyl, oleyl, ricinoleyl, behenyl, and erucyl alcohols, as well as 2-octyl dodecanol, are examples of satisfactory fatty alcohols.
10. Fatty alcohol ethers. Ethoxylated fatty alcohols of 10 to 20 carbon atoms include the lauryl, cetyl, stearyl, isostearyl, oleyl, and cholesterol alcohols having attached thereto from 1 to 50 ethylene oxide groups or 1 to 50 propylene oxide groups.
11. Ether-esters such as fatty acid esters of ethoxylated fatty alcohols.
12. Collagen, lanolin and sterol and derivative thereof, including lanolin oil, lanolin wax, lanolin alcohols, lanolin fatty acids, hydrogenated lanolin, and ethoxylated, propoxyated and acetylated derivatives thereof, and liquid and semisolid lanolin absorption bases are illustrative of emollients derived from lanolin. Also included in this group are sterols. Cholesterol and cholesterol fatty acid esters are examples thereof.
13. Polyhydric alcohols and polyether derivatives exemplified by propylene glycol, dipropylene glycol, dipropylene glycols 2000 and 4000, polyoxyethylene polyoxypropylene glycols, glycerol, sorbitol, ethoxylated sorbitol, polyethylene glycols 200-6000, poly(ethylene oxide) homopolymers (100,000-5,000,000), polyalkylene glycols and derivatives, 1,3-butylene glycol, 1,2,6-hexanetriol, ethohexadiol USP (2-ethyl-1,3-hexanediol), C15-C18 vicinal glycol, and polyoxypropylene derivatives of trimethylolpropane and the fatty esters (C10-C20) thereof.
14. Phospholipids, such as lecithin and derivatives.
15. Amides such as fatty acid amides, ethoxylated fatty acid amides, solid fatty acid alkanolamides.

Particularly useful moisture retaining emollients are glycerol, hexanetriol, butanetriol, lactic acid and its salts, urea, pyrrolidone carboxylic acid and its salts, amino acids, guanidine, diglycerol and triglycerol.

Various water-soluble or dispersible solvents and materials may also be present in the compositions of this invention wherein the total water phase is from about 50% to about 85% of the total composition weight. These include water, ethanol, isopropanol, hyaluronic acid and its salts, humectants, such as glycerol, sorbitol, propylene glycol, polyethylene glycol (220-600), polypropylene glycol (425-2025), alkoxylated glucose and hexanetriol, polyvinyl alcohol, butylene glycol(s), salts, and clays such as Veegum® (magnesium aluminum silicate, R. T. Vanderbilt, Inc.); soluble proteins and polypeptides; preservatives such as the methyl, ethyl, propyl and butyl esters of hydroxybenzoic acid (Parabens-Mallinckrodt Chemical Corporation), EDTA, methylisothiazolinone and imidazolidinyl ureas (Germall 115—Sutton Laboratories) phenoxyethanol (diocide-Diow) chlorophenesin; and an alkaline agent such as sodium hydroxide or potassium hydroxide to neutralize, if desired, part of the fatty acids or thickener which may be present, and botanical extracts.

A wide variety of conventional sunscreening agents are suitable for use in the present invention. Segarin, et al., at Chapter VIII, Pages 189 et seq., of Cosmetics Science and Technology, disclose numerous suitable agents, the disclosure of which is incorporated herein by reference. Specific suitable sunscreening agents include, for example:

p-aminobenzoic acid, its salts and derivatives, anthranilates, salicylates, cinnamic acid derivatives, dihydroxycinnamic acid derivatives, trihydroxycinnamic acid derivatives, hydrocarbons, dibenzalacetone and benzalacetophenone, naphthosulfonates, dihydroxynaphthoic acid and its salts, o- and p-hydroxy-biphenyldisulfonates, coumarin derivatives, diazoles quinine salts, quinoline derivatives, hydroxy or methoxy substituted benzophenones, uric and vilouric acids, tannic acid and its derivatives, hydroquinone, benzophenones, and the like.

Various vitamins may also be included in the compositions of the present invention. For example, Vitamin A and derivatives thereof, Vitamin B2, biotin, pantothenic acid, Vitamin D, Vitamin E and mixtures thereof may be used and niacin and derivatives. Myristal nicotinate is a preferred niacin derivative.

If desired, anti-inflammatories can be included in the compositions of the invention to enhance photoprotection benefits, particularly from UVA. Steroidal anti-inflammatories can be represented by hydrocortisone; non-steroidal anti-inflammatories by the oxicans, salicylates, acetic acid derivatives, fenamates, propionic acid derivatives, pyrazoles, substituted phenyl compounds, 2-naphthyl containing compounds, and the natural anti-inflammatory group illustrated by aloe vera. These are more fully outlined in U.S. Pat. No. 5,487,884, the entire contents of which are incorporated herein by reference.

The composition herein can also contain conventional cosmetic adjuvants and antioxidants. Representative antioxidants include ascorbic acid, Vitamin E, tocopheryl acetate, betaglucan, coenzyme Q10, butylated hydroxytoluene (BHT), superoxide dismutase and the like. Adjuvants include estradiol; progesterone; pregnanalone; coenzyme Q10; methylsolanomethane (MSM); copper peptide (copper extract); plankton extract (phytosome); glycolic acid; kojic acid; ascorbyl palmitate; all trans retinol; azaleic acid; salicylic acid; broparoestrol; estrone; adrostenedione; and androstanediols. Also included are dyes, opacifiers (e.g., titanium dioxide, zinc oxide), pigments, mica, perfumes, elastin, hydrolysates, epidermal growth factor, soybean saponins, mucopolysaccharides, *Centella asiatica*, Portulaca extract, tea tree oil, grape seed extract, ginseng, *ginko biloba*, green tea extract, yeast extract, allantoin, idebenone, retinyl palmitate, gamma aminobutyric acid, barium sulfate and soft focus powders, like nylon, silica, urethane and PMMA.

Controlling the pH of the composition ensures that the peptide and botanical extract are not degraded. The pH of the liquid phase is formulation dependent and preferably maintained at 4.5-8.5 and more near the skin pH balance of around 5.5. Any cosmetically or pharmaceutically acceptable pH adjusting or buffering compounds can be used. Preferred are triethanolamine, sodium hydroxide and ammonium hydroxide.

The product of the invention can be prepared using good manufacturing techniques involved in the mixing and blending of cosmetic. Preferably, organic ingredients, such as the emulsifiers, the sunscreens, the emollients, stabilizers and organosoluble preservatives are emulsified in water along with any organoclay material. To this emulsion can be added the remaining ingredients and finally the pH can be adjusted to the desired level. While the compositions of the invention can be made generally in any order, it is preferred that the C2-C22 acyl oligopeptide is first solubilized in dimethylisosorbide or ethoxydiglycol prior to the addition of any remaining oil phase ingredients. Mixing conditions such as temperature are within the grasp of the skill artisan. Some or all of the ingredients for the aqueous phase can be blended and then emulsified as desired.

A preferred topical cosmetic composition for treating wrinkled skin according to the present invention comprises:
  about 0.5% by weight of a cosmetically effective combination of the C2-C22 acylated oligopeptide of 3 to 20 amino acid units, fulvic acid, and optionally colloidal gold having a particle size in the millimicron range; and the balance
  one or more cosmetically acceptable ingredients including emulsifiers, penetration enhancers, emollients, solvents, adjuvants, and antioxidants.

The preferred weight ratio for the C2-C22 acylated oligopeptide and the fulvic acid is 0.01:1 to 1:1, more preferably 0.1:1 to 1:1, and most preferably 0.5:1. When colloidal gold is also included in the cosmetically effective combination of ingredients, the weight ratio of all three cosmetically effective ingredients is preferably 0.1:1:0.0001 to 1:1:0.1, more preferably 0.1:1:0.001 to 1:1:0.1, most preferably 0.5:1:0.02.

The following examples are for illustrative purposes only and are not intended to limit the scope of the claimed invention.

Extracellular matrix provides skin with the texture, elasticity and resilience. Active materials stimulating skin matrix are of great value for skin care health and appearance. Fulvic acid is obtained from JH biotech, Ventura, Calif. as a 3% aqueous solution and palmitoyl hexapeptide-6 is obtained from Helix Biomedix, (Bothell, Wash.). Colloidal gold was obtained from Grant Industries Inc, (Elmwood Park, N.J.) as a 0.1% gold solution in the product Colloid PMG-WP. These materials were tested together for matrix-rebuilding activity and were surprisingly found to provide a high level of activity as will be delineated in the following examples.

EXAMPLE 1

Loose Powder Cosmetic

| Ref: RD-1071 | Wt % |
|---|---|
| Mica | 58.4 |
| Barium Sulfate | 5.0 |
| Fumed Silica | 15.00 |
| Gold Colloid PMG-WP | 0.005 |
| Ethoxydiglycol | 6.45 |
| Palmitoyl hexapeptide-6 | 0.15 |
| Fulvic Acid | 10.0 |

This formula is made to be preservative free to ensure that the cosmetic was not cytotoxic during cellular testing. The final formula contained 0.005% elemental gold, 0.15% peptide and 0.3% fulvic acid on a weight % basis for these active ingredients.

EXAMPLE 2

Stimulation of the Mitochondrial Metabolic Activity

In order to maintain youthful appearance, skin needs to constantly replace and regenerate its damaged components. This is predominantly the role of dermal fibroblasts. How well this job is done depends on the metabolic vigor of these cells as damaged or dormant fibroblasts will not be able to actively produce the replacement parts for the skin. This is why the stimulation of their metabolic activity is viewed as beneficial to the skin, not unlike the stimulation of metabolic activity is beneficial to the muscle. We tested the effect of RD1071 on the metabolic activity of mitochondria of human dermal fibroblast cultures using MTT method (Berridge et al., 1993). Mitochondria are cellular powerhouses producing energy (ATP) for the entire cell. Example 1 formula (RD1071) showed a bell-shape stimulatory pattern, with the maximum effect (over 50% stimulation) at concentration of 0.5%. Thus, example 1 (RD1071) increases cellular metabolism in a dose-dependant manner. The positive control in this experiment is use of basic fibroblast growth factor, bFGF at 10 ng/ml concentration.

| Example 2 | Concentration % (v:v) | Mitochondrial Metabolism % Control | SEM (Error) |
|---|---|---|---|
| H20 (control) | 0.000 | 100 | 3.935 |
| bFGF | 10 ng/ml | 174 | 7.273 |
| RD1071 | 5.000 | 118 | 13.885 |
| RD1071 | 0.500 | 151 | 3.463 |
| RD1071 | 0.050 | 106 | 10.138 |
| RD1071 | 0.005 | 108 | 21.405 |

EXAMPLE 3

Protein Production Stimulation

The stimulation of metabolic activity by RD1071 also translated into an increase of total protein content in fibroblast cultures. This further demonstrates the beneficial effect of this test material. For example, UV radiation and aging are associated with the increased proteolytic activity in the skin. The stimulation of total protein production could counterbalance the loss of proteins caused by this increased proteolytic activity. Total protein was measured using the method of Skehan et al. (1990). Result shows that the metabolic stimulation by RD1071 detected in Example 2 also results in increased total protein contents in dermal fibroblast populations. Importantly, the patterns of stimulation of cellular metabolism and protein production are similar, which suggests that both activities are related. The basic fibroblast growth factor, bFGF, was again used as a positive control. The Example 1 composition at 0.5% significantly outperformed the basic fibroblast growth factor control.

| Example 3 | Concentration % (v:v) | Protein Stimulation % Control | SEM (error) |
|---|---|---|---|
| H20 (control) | 0.000 | 100 | 1.92 |
| bFGF | 10 ng/ml | 118 | 1.02 |
| RD1071 | 5.000 | 113 | 4.70 |
| RD1071 | 0.500 | 127 | 1.40 |
| RD1071 | 0.050 | 112 | 2.62 |
| RD1071 | 0.005 | 111 | 2.45 |

EXAMPLE 4

Of the proteins secreted by dermal fibroblast tissue, type I collagen is a major component of the skin. Production of dermal collagen decreases during aging. However, collagen is a macromolecule not readily absorbed by the skin, which may render such cosmetic products containing animal derived collagen ineffective with regard to improving collagen content in the skin. In contrast, it is much more beneficial to formulate cosmetic products with actives, which are easily absorbed by the skin, that stimulate endogenous collagen, in situ. Type I collagen assay (Zhao et al., 2005[1]) reveals that Example 1 composition at 0.5% increased Type 1 collagen by over 15% compared to the H2O control.

[1] Zhao H, Alexeev A, Chang E, Greenburg G, and Bojanowski K. Lycium barbarum glycoconjugates: effect on whole skin and cultured dermal fibroblasts. Phytomedicine, 2005; 12:132.

---

We claim:

1. A cosmetic composition for treating wrinkled human skin by rebuilding a dermal fibroblast matrix in human skin comprising:
   - (a) about 0.5% by weight of a cosmetically effective combination of the following:
     - (i) 0.15% by weight of palmitoyl-substituted hexapeptide-14 having SEQ. ID NO: 1 where the C-terminal is a carboxamide terminal;
     - (ii) 0.3% by weight fulvic acid; and
     - (iii) 0.005% by weight colloidal gold; and
   - (b) one or more cosmetically acceptable ingredients selected from the group consisting of emulsifiers, penetration enhancers, emollients, solvents, adjuvants, and antioxidants.

2. A method of treating a patient having wrinkled skin by rebuilding a dermal fibroblast matrix in human skin, which comprises the step of topically administering to the patient on the wrinkled skin, a cosmetically effective amount of the cosmetic composition defined in claim 1 to rebuild the dermal fibroblast matrix in the patient's wrinkled skin.

* * * * *

SEQUENCE LISTING

```
<160> NUMBER OF SEQ ID NOS: 2

<210> SEQ ID NO 1
<211> LENGTH: 6
<212> TYPE: PRT
<213> ORGANISM: Artificial
<220> FEATURE:
<223> OTHER INFORMATION: synthetic sequence
<220> FEATURE:
<221> NAME/KEY: MOD_RES
<222> LOCATION: (6)..(6)
<223> OTHER INFORMATION: AMIDATION
<220> FEATURE:
<221> NAME/KEY: MOD_RES
<222> LOCATION: (6)..(6)
<223> OTHER INFORMATION: AMIDATION, N-ACYLATION

<400> SEQUENCE: 1

Phe Ala Leu Leu Lys Leu
1               5

<210> SEQ ID NO 2
<211> LENGTH: 6
<212> TYPE: PRT
<213> ORGANISM: Artificial
<220> FEATURE:
<223> OTHER INFORMATION: Synthetic sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: AMIDATION
```

```
<400> SEQUENCE: 2

Glu Glu Met Gln Arg Arg
1               5
```